(12) United States Patent
Saliga

(10) Patent No.: US 11,406,819 B1
(45) Date of Patent: Aug. 9, 2022

(54) HIGH ENERGY IONTOPHORESIS METHOD FOR RAPID TRANSDERMAL DISINFECTION

(71) Applicant: Thomas Saliga, St Petersburg, FL (US)

(72) Inventor: Thomas Saliga, St Petersburg, FL (US)

( * ) Notice: Subject to any disclaimer, the term of this patent is extended or adjusted under 35 U.S.C. 154(b) by 0 days.

(21) Appl. No.: 17/737,440

(22) Filed: May 5, 2022

Related U.S. Application Data

(60) Provisional application No. 63/259,188, filed on Jun. 28, 2021.

(51) Int. Cl.
| | | |
|---|---|---|
| *A61N 1/30* | (2006.01) | |
| *A61K 33/38* | (2006.01) | |
| *A61N 1/04* | (2006.01) | |
| *A61K 9/00* | (2006.01) | |
| *A61K 33/18* | (2006.01) | |

(52) U.S. Cl.
CPC ............ *A61N 1/303* (2013.01); *A61K 9/0009* (2013.01); *A61K 33/18* (2013.01); *A61K 33/38* (2013.01); *A61N 1/0432* (2013.01)

(58) Field of Classification Search
CPC ..... A61N 1/30; A61L 2/02; A61L 2/16; A61L 2101/00; A61L 2202/00; A61K 9/0009
See application file for complete search history.

*Primary Examiner* — Deanna K Hall
(74) *Attorney, Agent, or Firm* — Larson & Larson, P.A.; Frank Liebenow; Justin P. Miller

(57) ABSTRACT

A system, method, and apparatus for rapid transdermal disinfection includes a processor or equivalent that generates a series of pulses having pulse widths limited to less than two microseconds. The pulses are amplified to a direct-current voltage of between 150 volts and 500 volts and connected to a positive electrode for attaching to an animal. A negative electrode for attaching to the animal is electrically connected to a current limiter for limiting electrical current flow between the positive electrode and the negative electrode to between 0.2 amps and 2 amps.

20 Claims, 4 Drawing Sheets

HIGH ENERGY IONTOPHORESIS METHOD FOR RAPID TRANSDERMAL DISINFECTION

CROSS-REFERENCE TO RELATED APPLICATION

This application claims the benefit of U.S. provisional application No. 63/259,188 filed on Jun. 28, 2021, the disclosure of which is incorporated by reference.

FIELD

This invention relates to the field of electronic skin treatment and more particularly to a system for providing high-voltage pulses to the skin at select frequencies.

BACKGROUND

There is a need for a portable, rapid, non-invasive, locally-applied, transdermal disinfection system to treat subcutaneous infections from ticks, mosquito bites, parasites and the like with little or no user discomfort. Further, it desired that this system has a completely automatic protocol such that non-medically trained persons can apply it with consistent results.

Alcohol, silver, and iodine compounds are well known topical disinfectants but have a limited perfusion beneath a skin's surface. Likewise, ultraviolet disinfection lamps can penetrate mammal skin a limited distance but are potentially harmful to eyes and healthy tissues. A method was then sought which could introduce proven disinfectants trans-dermally for the treatment of underlying infections without puncturing the skin with needles and the like. Skin penetrating solvents such as dimethylsulfoxide (DMSO) combined with iodine compounds have been considered but the ability to co-transport the iodine was difficult to measure and confirmation of effectiveness difficult.

Iontophoresis is a well-known method for drug delivery by the use of a relatively low voltage gradient on the skin. Molecules are transported across the stratum corneum by electrophoresis and electroosmosis. However, due to the low currents used, transport is slow. A faster method was needed.

It is well known that swimming pool water can be disinfected by electrolysis of dissolved salts which releases chlorine and other gases. Chlorine and nascent oxygen are typically among the gases released. Both are well-known disinfectants.

As noted above, topical disinfectants (alcohol-based, silver-based, iodine-based, etc.) typically have little or quite slow perfusion to subcutaneous underlying tissues. Without somehow being introduced transdermally, such topical disinfectants are of little immediate help when a rapid subcutaneous disinfection is required.

Antibiotics such as the entire class of penicillin's are ingested orally and are of no immediate help and are not effective as a localized infection solution. It may be practical to inject an antibiotic using a needle and syringe but this is not painless and not typically performed without a trained medical professional.

Ultraviolet disinfection lamps can penetrate skin a limited distance but are potentially harmful to eyes and healthy tissues also. Laser therapy technology is expensive and not safe enough for untrained persons to operate.

Standard methods of Iontophoresis offer a near ideal modality for disinfectant transdermal delivery but conventional approaches using low voltage galvanic currents are far too slow for rapid disinfection. A better suited version of Iontophoresis uses high voltage pulsed current. High voltage pulsed current has been used in therapy since the 1940's. The modality employs a single polarity pulsed current delivered as a doublet with applied voltages in the 150V to 500V range. Pulse widths are typically less than 200 microseconds but more than 5 microseconds. The doublet repetition rate is so low that only microampere average currents flow, on average. Non-the-less, each pulse group causes significant nerve excitation with resultant discomfort for the user. Typically, the user or attending medically trained person must manually adjust the applied voltage to achieve suitable results.

None of the existing methods offer non-invasive, rapid, portable, discomfort-free and selective area trans-dermal disinfection nor are they capable of being administered by medically untrained persons.

What is needed is a system and method that will provide non-invasive, rapid, portable, discomfort-free trans-dermal disinfection.

SUMMARY

A method and system for high voltage pulsed current for the disinfection and pain relief of insect bites and other subcutaneous infection is disclosed. In actual testing on human insect bites, the method and system achieved all objectives with only three minutes of application on the infected area. Further, application was performed with minimal instruction to the operator of the device. The same high voltage pulsed current as disclosed below was used on a canine having multiple stings as well.

The claimed system applies single-polarity electric pulses to the patient using conventional iontophoresis electrodes. In some embodiments, the single-polarity electric pulses:
  a) are provided at a variable pulse rate, current-limited to produce an average DC current that does not exceed 2 mA.
  b) have pulse widths that are either fixed or variable.
  c) are always less than 2 microseconds.
  d) produce a current at the electrodes that is substantially constant with a peak current from 0.1 amps to 2 amps.
  e) are delivered for a predefined application time.
  f) optionally, are delivered in conjunction with a sub-electrode disinfectant is provided such as alcohol, an alcohol compound, a silver compound, iodine or an iodine compound.

By use of high current and short current pulses, not only are topically applied disinfectants driven trans-dermally at a faster rate, but the current density under the electrodes is sufficient to cause micro-electrolysis of underlying Interstitial fluids. Depending on the dissolved salts, both nascent oxygen and chlorine bubbles are released by such micro-electrolysis, leading to further, rapid disinfection. The pulse-current multiplied by the pulse width is managed to a level that is below that which causes nerve excitation, therefore reducing or eliminating any pain from the application.

In one embodiment, a system for rapid transdermal disinfection is disclosed including a device for generating a series of pulses having a width of each pulse limited to be less than two microseconds connected to a device for amplifying each of the series of pulses to an amplitude of a direct-current voltage of between 150 volts and 500 volts. The system includes a device for limiting a current of the amplified pulses to a current of between 0.2 amps and 2 amps and devices for applying the amplified pulses to a skin of an animal for rapid transdermal disinfection.

In another embodiment, a method for rapid transdermal disinfection is disclosed including generating a set of pulses for a period of time. Each pulse in the set of pulses has a direct current amplitude of between 150 volts and 500 volts at a maximum current of less than 2 mA and each pulse has a maximum pulse width of two microseconds, such that an average current output is greater than 0.2 A and less than 2 A. The method includes applying the set of pulses to a skin of an animal, thereby transdermally treating an infection.

In another embodiment, an apparatus for rapid transdermal disinfection is disclosed including a processor that generates a series of pulses having pulse widths limited to less than two microseconds. An amplifier is connected to the processor and receives the series of pulses, amplifying each pulse in the series of pulses to a direct-current voltage of between 150 volts and 500 volts. An output of the amplifier is connected to a positive electrode for attaching to an animal. A negative electrode for attaching to the animal is electrically connected to a current limiter, the current limiter limiting electrical current flow between the positive electrode and the negative electrode to between 0.2 amps and 2 amps.

BRIEF DESCRIPTION OF THE DRAWINGS

The invention can be best understood by those having ordinary skill in the art by reference to the following detailed description when considered in conjunction with the accompanying drawings in which.

DETAILED DESCRIPTION

Figure 1:
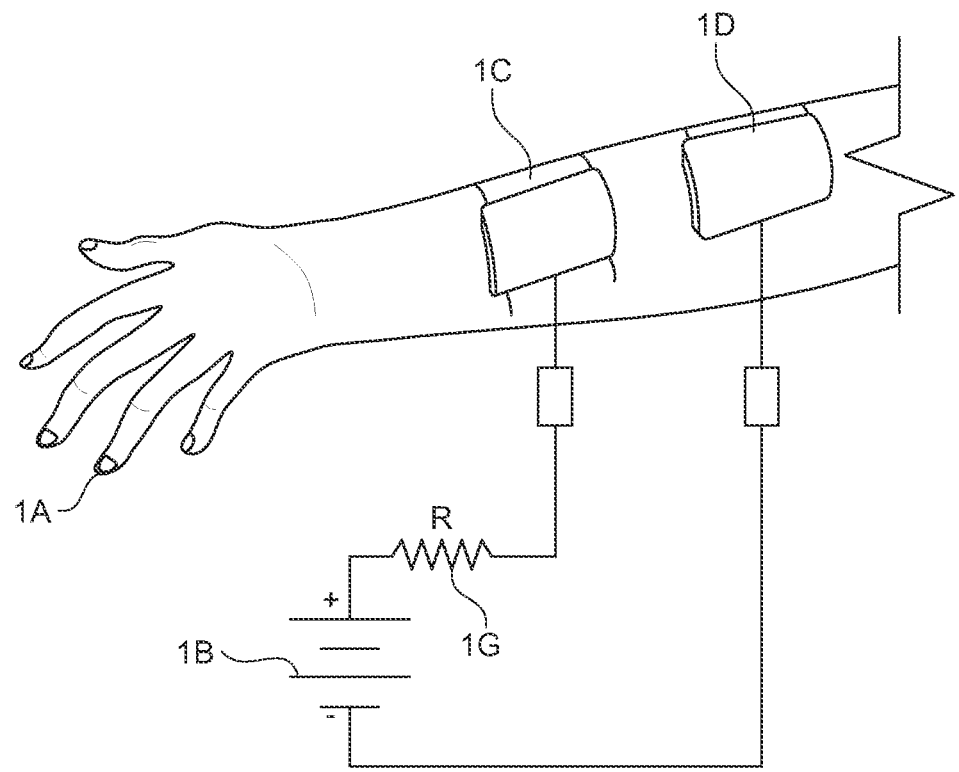
FIG. 1 shows application of conventional electrodes to a human appendage and its connection to a controlled-current unipolar voltage generator

Reference will now be made in detail to the presently preferred embodiments of the invention, examples of which are illustrated in the accompanying drawings. Throughout the following detailed description, the same reference numerals refer to the same elements in all figures.

FIG. 1 shows a simple iontophoresis system as applied to animal tissue 1A such as a human arm. Low voltage source 1B drives a current through a current limiting resistor 1G into attached conductive electrodes 1C/1D. Optionally, in some embodiments, a disinfectant is placed under either the positive electrode 1C or the negative electrode 1D for transcutaneous transport. Such transport depends upon the disinfectant's active chemical, in particular, the molecular polarity of this active chemical.

For example, if a topical antiseptic is to be transported, the topical antiseptic is placed between the positive electrode 1C and the human arm 1A for deeper treatment. Similarly, if an iodine compound such as povidone-Iodine is to be transported to an underlying infection 2E as in FIG. 2, then the negative electrode 1D is preferably placed over the iodine compound.

Figure 2:
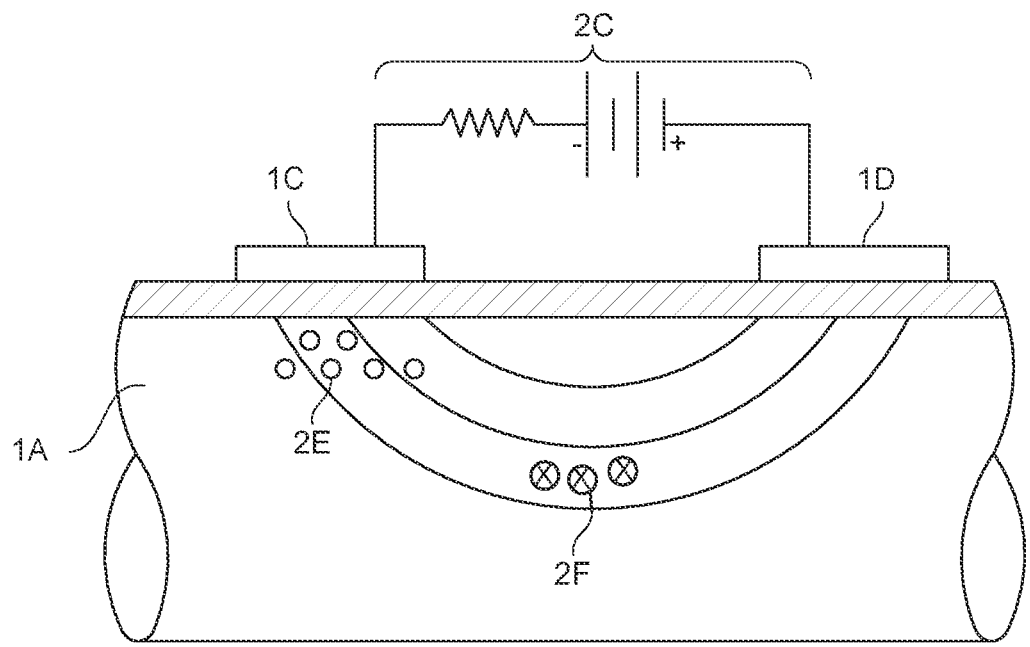
FIG. 2 is a cross section of human tissue showing a sub-cutaneous infection and electrical current flow.

FIG. 2 shows a subcutaneous infected region 2F being treated by a prior iontophoresis system 2C with electrodes 1C/1D. The flow of electric current between the electrodes 1C/1D, through the animal tissue 1A release ions and/or micro-bubbles of gas 2F that are released due to electrolytic reaction with interstitial fluids. While this simple iontophoresis provides a low voltage, it requires a long application time of 20 minutes or more of subcutaneous tissue electric current flow. Instead, a rapid treatment is desired. For example, treatment of common insect infections from mosquitos and the like are preferred to have shorter application times (e.g., shorter than 20 minutes) as the patient often has several or a multitude of such bites. Unfortunately, an increase in drive voltage will speed up a disinfectant chemical's transport, but will result in electrical shock issues to the patient, for example, pain.

Figure 3:
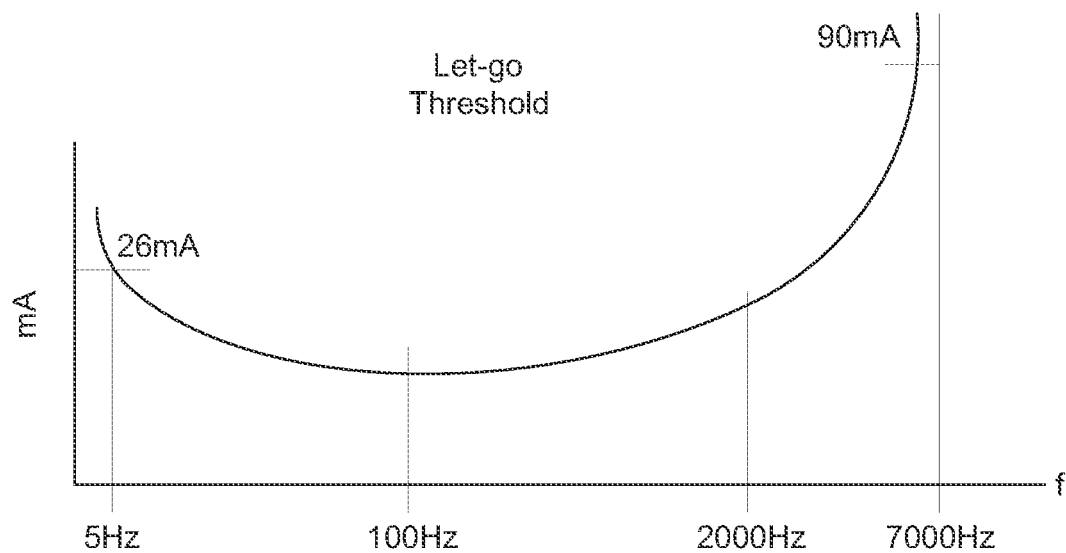
FIG. 3 is a partial shock level sensitivity curve for humans vs. applied frequency.

Electrical shock sensitivity curves are well-known from electrical safety studies. FIG. 3 sketches a shock "let-go" curve versus applied frequency and current. Note that frequencies above about 7000 Hz become even less of a shock hazard (e.g., requiring over 90 ma before the human "lets go.". Prior Electro-Surgery Units (ESU) take advantage of this phenomena to apply quite high voltages and currents to tissues without nerve excitation. If the electrical pulse width is very short, the sodium-potassium nerve membrane transport period is not exceeded. In this, the pulse is either bipolar or unipolar without the nerve firing and, therefore, limiting sensation or pain. Uni-polar pulse rate however must be low enough such that the average DC current does not exceed the DC shock threshold.

Figure 4:
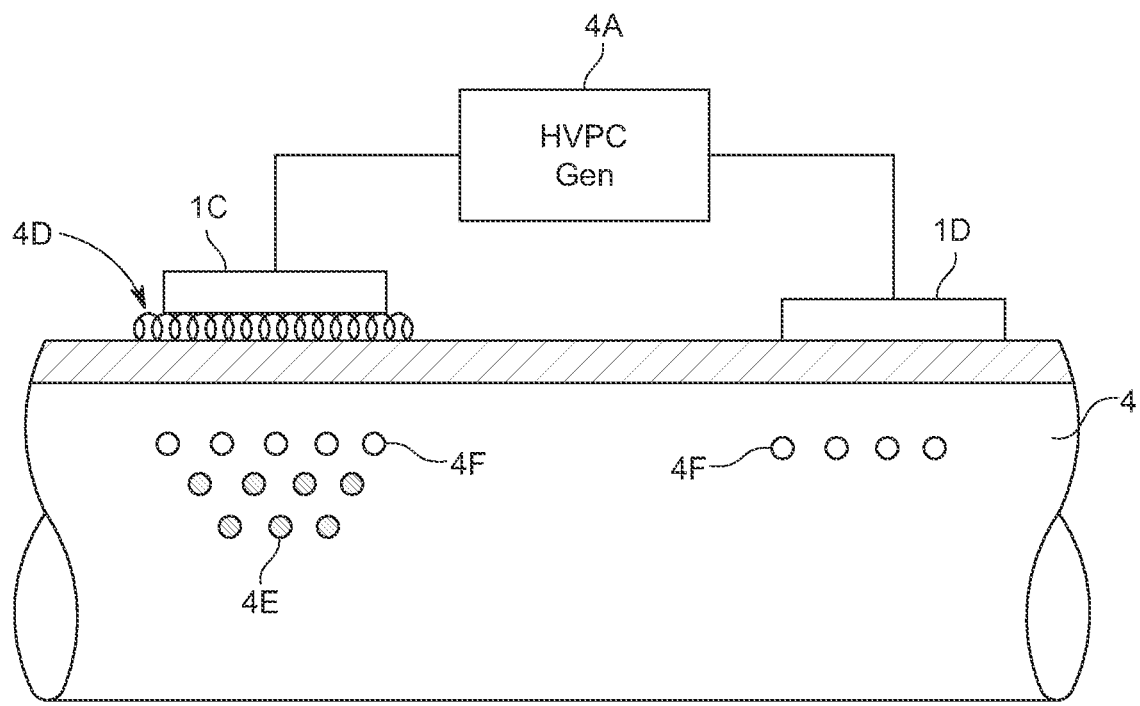
FIG. 4 shows a cross section of infected human tissue with electrophoresis driven drug disinfecting and microelectrolysis release of gases from interstitial fluids.

A branch of electrophysiology called High Voltage Pulsed Current (HVPC) takes advantage of the above by applying voltages as high as 500V with dual-short pulses. These pulses are typically in the 5 microseconds to 200 microseconds range. Application of such requires medically trained personnel to apply electrodes 1C/1D as in FIG. 4 and connect the electrodes 1C/1D to a prior-HVPC generator 4A (see FIG. 4). A mammal appendage 4 has electrodes 1C/1D applied with a preferred polarity to the prior-HVPC generator 4A. A drug or disinfectant chemical 4D is placed under the preferred polarity of the electrodes 1C/1D. Upon operation of the prior-HVPC generator 4A, high voltage pulses transport, in bursts, the disinfectant chemical 4D transdermally. In this figure, the infection 4E is treated subcutaneously by an antiseptic 4D. Ions of antiseptic 4D are driven transcutaneously and micro-bubbles of gas 4F may be released due to electrolytic reaction with interstitial fluids. Iodine is one example of such an antiseptic 4D and when iodine is used, the iodine is disposed on the skin beneath the negative electrode 1C. Silver impregnated paste is another example of such an antiseptic 4D and when silver impregnated paste is used, the silver impregnated paste is disposed on the skin beneath the positive electrode 1D.

The prior-HVPC 4A transports the drug or disinfectant chemical 4D sub-dermally faster than the low voltage electrophoresis method of FIGS. 1 and 2. However, use of the prior-HVPC generator 4A must be performed by a trained professional and requires careful adjustment of voltage and pulse pair repetition rate. Further, without careful adjustment, the typically 100 microsecond wide pulses cause considerable nerve pain and discomfort.

The rapid transdermal disinfection system 7 (see FIG. 7) delivers very short, unipolar pulses in the range of 0.1 microseconds to 1.5 microseconds of pulse widths via electrodes 1C/1D to human appendages with peak currents in the range of 0.1 ampere to 2 ampere, resulting in little or insubstantial pain as the average current is less than 2 milliamperes (mA). The average current as calculated by the on-time of the pulse multiplied by the peak current is maintained below a defined value (e.g., 2 milliamperes) resulting in little or no shock perception to the patient.

Figure 5:
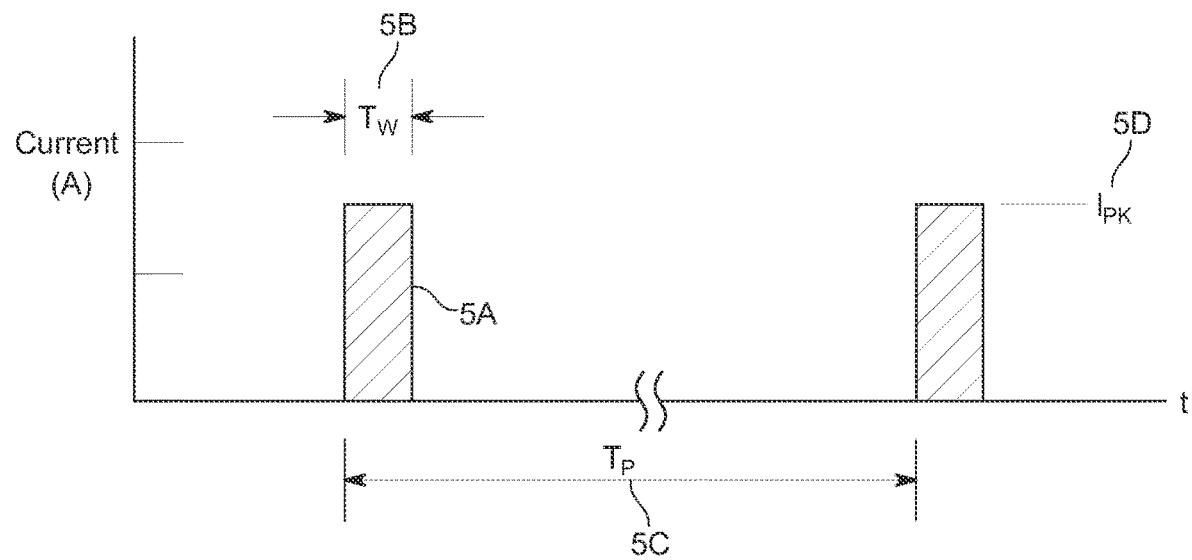
FIG. 5 shows a time versus electrical current flow plot of a preferred waveform.

Precise current limiting of an applied pulse is provided by the rapid transdermal disinfection system 7 connected to electrodes 1C/1D. Each pulse is a simple binary pulse. FIG. 5 shows a preferred pulse waveform. Each pulse 5A has time width 5B of Tw and repetition period 5C of Tp. The peak applied current 5D is Ipk.

The ((Tw/Tp)×Ipk) current is controlled to be nearly undetectable by normal human nerves when applied to human skin by electrodes 1C/1D, for example, electrodes having one square inch or more of surface area. The maximum pulse repetition rate is then calculated such that a very low shock level is achieved. For example, if average dc current shock level is set to 0.5 mA (Iavg) and Tw=0.75 microseconds. and Ipk=0.3 A, then the pulse rate in pulses per second is less than:

$$\text{Pulse Rate(max)} = Iavg/(Ipk*Tw) = 0.0005A/(0.3A \times 0.75 usec) = 2222 pps.$$

Figure 6:
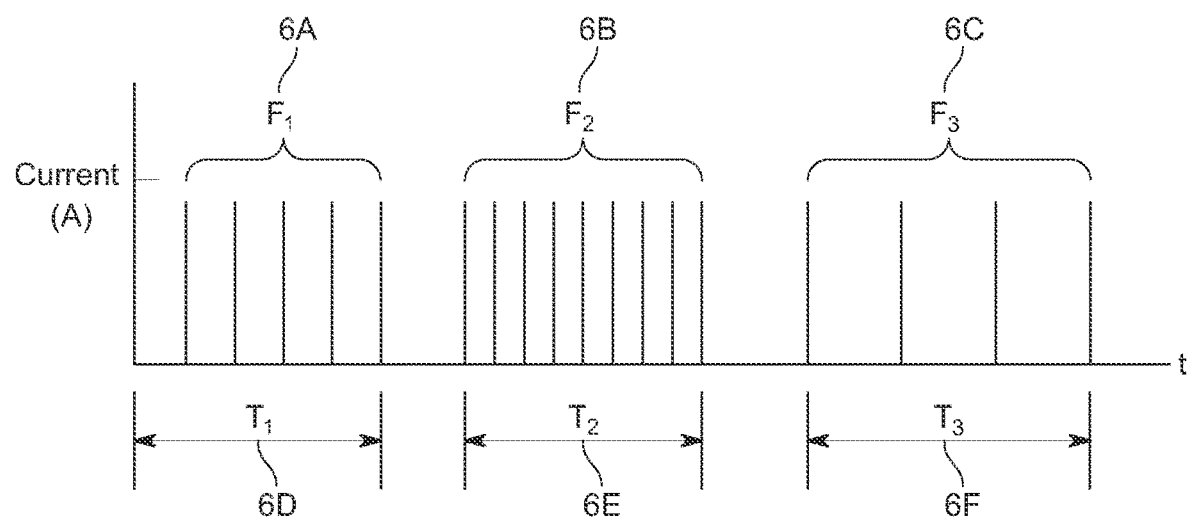
FIG. 6 shows a method for enhanced disinfection using a sequence of pathogen antagonistic pulse rates.

There is published research suggesting that certain applied electrical frequencies can enhance healing effects and/or anti-pathogenic effects. For instance, 528 Hz is believed to be a DNA healing frequency. It was reasoned that, provided the maximum allowable pulse rate was not exceeded, that adjusting the applied pulse rate to one or more of these frequencies could be beneficial. FIG. 6 shows a time plot of such a method. A first pulse rate F1 (6A) is applied to the electrodes 1C/1D for period T1 (6D). Subsequently and similarly, two additional frequencies are generated for their own respective periods. Total treatment time is the sum (T1+T2+T3).

Figure 7:
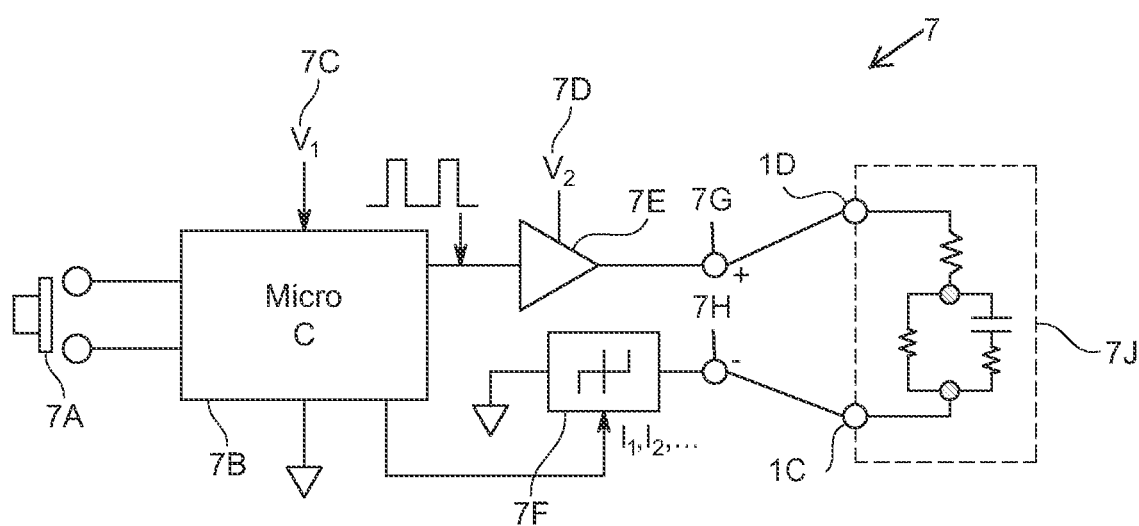
FIG. 7 is a functional schematic of an electronic circuit that provides the requisite high voltage pulsed current.

FIG. 7 is a functional diagram of the rapid transdermal disinfection system 7. A microcontroller 7B is programmed to output pulses to an amplifier 7E when pushbutton switch 7A (or any other switch) is closed. Logic voltage supply 7C powers the microcontroller 7B. A higher voltage supply 7D, typically in the 250V to 500V range, powers the amplifier 7E. In some embodiments, the pulses are produced by the microcontroller 7B in the protocol depicted in FIG. 6. The amplifier 7E receives pulses from the microcontroller and amplifies the pulses to high voltage levels, creating amplified pulses. The amplified pulses are presented across nodes 7G/7H, the active node 7G providing the positive polarity and the return node 7H is the return for the current and is connected through a current limiting circuit 7F which, in some embodiments, is adjustable to limit peak current to any of several different peak current values. The active node 7G is connected to the positive electrode 1D and the return node 7H is connected to the negative electrode 1C and, when the positive electrode 1D and negative electrode 1C are installed on an animal, a biological load 7J is formed having a certain equivalent capacitance and resistance well known in the art.

In operation, the total treatment period is set, for example, set to three minutes, generating the above pulse parameters through software programing of the microcontroller 7B. It is anticipated that, in some usage scenarios, silver paste, lidocaine and/or povidone-iodine are applied to the affected skin area before application of electrodes 1C/1D.

Note that by pre-setting the pulse parameters of the generator (Tw, Ipk, Tp) and setting the total treatment period, the user does not require special training. The user need only assure that a proper disinfectant has been placed on the affected skin area, attach the electrodes and close the pushbutton switch 7A. Thus, persons untrained in formal HVPC iontophoresis procedures easily learn and apply this method for insect bites and the like with no shock hazard.

Note that the rapid transdermal disinfection system 7 as shown in FIG. 7 is an example as it is known to implement processor-based systems using discrete components without processors and there are many anticipated electrical circuits that will produce the described high-voltage pulses at the disclosed timing and energy levels.

Equivalent elements can be substituted for the ones set forth above such that they perform in substantially the same manner in substantially the same way for achieving substantially the same result.

It is believed that the system and method as described and many of its attendant advantages will be understood by the foregoing description. It is also believed that it will be apparent that various changes may be made in the form, construction and arrangement of the components thereof without departing from the scope and spirit of the invention or without sacrificing all of its material advantages. The form herein before described being merely exemplary and explanatory embodiment thereof. It is the intention of the following claims to encompass and include such changes.

What is claimed is:

1. A system for rapid transdermal disinfection, the system comprising:
   means for generating a series of pulses, a width of each pulse limited to be less than two microseconds;
   means for amplifying each of the series of pulses, creating amplified pulses having a direct-current voltage of between 150 volts and 500 volts;
   means for limiting a current of the amplified pulses to a current of between 0.2 amps and 2 amps; and
   means for applying the amplified pulses to a skin of an animal.

2. The system of claim 1, wherein the means for generating the series of the pulses is a microcontroller, the microcontroller programmed to generate the series of the pulses at a set of frequencies for controlled time periods.

3. The system of claim 2, wherein the set of frequencies comprises 528 Hz.

4. The system of claim 1, wherein the means for applying the amplified pulses to the skin of the animal comprises electrodes.

5. The system of claim 4, further comprising a disinfectant applied between the skin of the animal and one of the electrodes.

6. The system of claim 5, wherein the disinfectant comprises silver and the disinfectant is applied between the skin of the animal and a positive polarity electrode of the electrodes.

7. The system of claim 5, wherein the disinfectant comprises iodine and the disinfectant is applied between the skin of the animal and a negative polarity electrode of the electrodes.

8. The system of claim 5, wherein the disinfectant comprises alcohol.

9. A method for rapid transdermal disinfection, the method comprising:
   generating a set of pulses for a period of time, each pulse in the set of pulses has a direct current amplitude of between 150 volts and 500 volts at a maximum average current of less than 2 mA, each pulse has a maximum pulse width of two microseconds, such that an peak current is greater than 0.2 A and less than 2 A; and applying the set of pulses to a skin of an animal, thereby transdermally treating an infection.

10. The method of claim 9, wherein in the step of generating, the set of pulses are generated at a frequency of 528 Hz.

11. The method of claim 10, wherein the step of applying the set of pulses to the skin of the animal comprise conducting the set of pulses through a pair of electrodes, each electrode of the pair of electrodes being stuck to the skin of the animal.

12. The method of claim 11, further comprising inserting a disinfectant between the skin of the animal and one of the pair of electrodes.

13. The method of claim 11, further comprising inserting a disinfectant comprising silver between the skin of the animal and a positive polarity electrode of the pair of electrodes.

14. The method of claim 11, further comprising inserting a disinfectant comprising iodine between the skin of the animal and a negative polarity electrode of the pair of electrodes.

15. The method of claim 11, further comprising inserting a disinfectant comprising alcohol between the skin of the animal and an electrode of the pair of electrodes.

16. An apparatus for rapid transdermal disinfection, the apparatus comprising:

a processor, the processor generates a series of pulses having pulse widths limited to less than two microseconds;

an amplifier receiving the series of pulses and amplifying each pulse in the series of pulses to an output having a direct-current voltage of between 150 volts and 500 volts;

a positive electrode for attaching to an animal, the positive electrode electrically connected to output of the amplifier;

a negative electrode for attaching to the animal; and a current limiter connected to the negative electrode, the current limiter limiting electrical current between the positive electrode and the negative electrode to between 0.2 amps and 2 amps.

17. The apparatus of claim 16, wherein a pulse rate of the pulses is 528 Hz.

18. The apparatus of claim 16, further comprising a disinfectant that comprises silver applied between a skin of the animal and the positive electrode.

19. The apparatus of claim 16, further comprising a disinfectant that comprises iodine applied between a skin of the animal and the negative electrode.

20. The apparatus of claim 16, further comprising a disinfectant that comprises alcohol applied between a skin of the animal either the positive electrode, the negative electrode or both.

* * * * *